United States Patent
Hiroshima

(10) Patent No.: US 6,791,319 B2
(45) Date of Patent: Sep. 14, 2004

(54) EDDY CURRENT PROBE WITH TRANSVERSE POLYGONAL DETECTING COIL

(75) Inventor: Tatsuo Hiroshima, Chiba (JP)

(73) Assignee: Marktec Corporation, Tokyo (JP)

( * ) Notice: Subject to any disclaimer, the term of this patent is extended or adjusted under 35 U.S.C. 154(b) by 0 days.

(21) Appl. No.: 10/260,521

(22) Filed: Oct. 1, 2002

(65) Prior Publication Data

US 2003/0132748 A1 Jul. 17, 2003

(30) Foreign Application Priority Data

Jan. 17, 2002 (JP) ........................................ 2002-009298

(51) Int. Cl.[7] .............................................. G01N 27/82
(52) U.S. Cl. ..................................... 324/240; 324/242
(58) Field of Search ........................ 324/228, 239–243, 324/260, 262

(56) References Cited

U.S. PATENT DOCUMENTS

| 1,960,028 | A | * | 5/1934 | Ricker ........................ 324/334 |
| 4,016,487 | A | * | 4/1977 | Neumaier ................... 324/232 |
| 4,594,549 | A | * | 6/1986 | Smith et al. ................ 324/232 |
| 4,604,574 | A | * | 8/1986 | Posluszny et al. ..... 324/207.12 |
| 4,853,604 | A | * | 8/1989 | McMullin et al. .......... 318/653 |
| 6,377,040 | B1 | * | 4/2002 | Hell ............................ 324/240 |
| 6,479,989 | B2 | * | 11/2002 | Taylor ........................ 324/219 |

FOREIGN PATENT DOCUMENTS

| JP | 57-173701 | * 10/1982 |
| JP | 62-140062 | 6/1987 |
| JP | 9-178710 | 7/1999 |
| JP | 2002-214202 | 7/2002 |
| JP | 2003-50234 | 2/2003 |
| JP | 2003-149209 | 5/2003 |
| JP | 2003-149210 | 5/2003 |

OTHER PUBLICATIONS

Karasawa et al., "A New Surface Eddy Current Probe Without Lift–Off Noise and With Phase Information on Flaw Depth" p. 131–132 of the Abstract of Fall Conference, Oct. 2–Oct. 4, 2001, of the Japanese Society for Non–Destructive Inspection/Discussed in the Specification, Summary of Fall Conference attached.

Development of New Eddy Current Probe with Lift–off Noise Free, Oct. 1999, pp. 111–112.

Koyama et al., "Investigation of Multi–Detection Coil®Probe," *Collected Papers of Symposium for Nondestructive Evaluation Using Thermograph*, pub. Nov. 2001; vol. 2001, pp. 67–72.

* cited by examiner

*Primary Examiner*—Jay Patidar
*Assistant Examiner*—Reena Aurora
(74) *Attorney, Agent, or Firm*—Armstrong, Kratz, Quintos, Hanson & Brooks, LLP

(57) ABSTRACT

An exciting coil is constructed by winding a winding in a groove formed on the outer circumference of a circular ring member, and a detecting coil in the shape of a polygon (such as a triangle and a pentagon) when seen from the front is positioned. One side of the detecting coil is placed in a diameter direction of the exciting coil, inside the exciting coil, and the vertex opposite to the one side is placed apart from the exciting coil so that the detecting coil is orthogonal to the exciting coil. A side surface of the exciting coil on the side opposite to the vertex is placed to face the surface of a test material, and used as a flaw detection surface.

11 Claims, 16 Drawing Sheets

EDDY CURRENT PROBE WITH TRANSVERSE POLYGONAL DETECTING COIL

BACKGROUND OF THE INVENTION

The present invention relates to an eddy current testing probe comprising an exciting coil and a detecting coil, for use in detection of surface flaws of a conductive test material.

An eddy current testing probe is used to detect surface flaws of conductive materials and products such as metals. FIG. 1 is a schematic view showing schematically the configuration of a conventional general eddy current testing probe. The conventional general eddy current testing probe comprises an exciting coil 1 in the shape of a circular ring, and a detecting coil 2 in the shape of a circular ring having the same diameter as the exciting coil 1. The exciting coil 1 and the detecting coil 2 are arranged parallel to each other, and a surface of the detecting coil 2 on the side opposite to the exciting coil 1 functions as a flaw detection surface. When using such an eddy current testing probe, the surface of a test material T, such as a conductive material and product, and the flaw detection surface are arranged to face each other with a suitable distance therebetween, the exciting coil 1 and the detecting coil 2 are positioned so that the center axis of the exciting coil 1 is substantially orthogonal to the surface of the test material T, and then an alternating current is caused to flow in the exciting coil 1. As a result, an AC magnetic field is generated around the exciting coil 1, and an eddy current is induced on the surface of the test material T by the AC magnetic field.

If there is a flaw on the surface of the test material T, the eddy current flows along the flaw. Therefore, when the eddy current testing probe is moved from a portion where no flaw is present to a portion where a flaw is present, the path of the eddy current changes. Accordingly, the strength and direction of a magnetic field caused by the eddy current vary, and a voltage between the terminals (output voltage) of the detecting coil 2 induced by this magnetic field changes. Since this voltage change is generally detectable as a change in the amplitude and phase of AC voltage, the amplitude and phase of the voltage between the terminals of the detecting coil 2 are measured, and the presence/absence and properties of flaw on the surface of the test material T are detected from the measured results.

Compared to other eddy current testing device such as a through coil that carries out an eddy current test by inserting a test material into a solenoid coil, an eddy current testing probe as mentioned above is applicable to various shapes of test materials and has a simple structure, and therefore it is used in a variety of fields. In such a conventional eddy current testing probe, however, the output of the detecting coil 2 contains a phase component due to the distance between the exciting coil 1 and the surface of the test material T, i.e., so-called lift-off, and a change in lift-off is detected as a noise component. Therefore, there are disadvantages that it is difficult to detect only a flaw and it is hard to adopt a phase analysis used for analyzing the properties of flaw such as the type and depth of the flaw.

The following description will explain an operational principle of the conventional eddy current testing probe. A voltage Vc between the terminals of the detecting coil 2 is expressed by the sum of a voltage Vex induced by a magnetic field generated by an exciting current Iex flowing in the exciting coil 1 and a voltage Vin induced by a magnetic field generated by an eddy current Iin.

$$Vc = Vex + Vin \tag{1}$$

Here, the voltages Vex and Vin can be expressed by equations (2) to (5).

$$Vex = A \cdot (d\phi ex/dt) \tag{2}$$

$$\phi ex = B \cdot Iex + \Phi 1(d) \tag{3}$$

$$Vin = C \cdot (d\phi in/dt) \tag{4}$$

$$\phi in = D \cdot Iin + \Phi 2(d) \tag{5}$$

where A, B, C, D: constants, $\phi ex$: the strength of the magnetic field generated by the exciting current Iex, $\Phi 1(d)$: a varying component of $\phi ex$ due to a change in lift-off d, $\phi in$: the strength of the magnetic field generated by the eddy current Iin, and $\Phi 2(d)$: a varying component of $\phi in$ due to a change in lift-off d.

Thus, when the lift-off d changes, since the magnetic fields $\phi ex$ and $\phi in$ vary accordingly, both of the amplitude and phase of the voltage Vc between the terminals of the detecting coil 2 change.

For such a reason, when the lift-off changes or the angle of the exciting coil 1 to the surface of the test material T changes, there occurs a change in the noise component and the phase component due to lift-off, contained in the output of the detecting coil 2 as described above. Therefore, conventionally, there has been used eddy current testing probes having a structure capable of scanning the surface of the test material T while maintaining constant lift-off, or a structure capable of measuring the amount of lift-off and correcting the output of the detecting coil 2 so as to remove the component due to lift-off from the output. Such eddy current testing probes have the problems of complicated structures and high prices.

In order to solve the problems, the following eddy current testing probe was proposed, and reported at p. 131 of the Abstract of Fall Conference, 2000, of the Japanese Society for Non-Destructive Inspection (hereinafter referred to as the "prior art reference"). FIG. 2 is a schematic view showing schematically the configuration of the eddy current testing probe reported in the prior art reference, and FIG. 3 is an explanatory view for explaining the operational principle of the eddy current testing probe. As shown in FIG. 2, this eddy current testing probe comprises an exciting coil 1 in the shape of a circular ring and a detecting coil 2 in the shape of a quadrangular ring, and the exciting coil 1 and the detecting coil 2 are positioned so that the center axis of the detecting coil 2 is orthogonal to the center axis of the exciting coil 1 in the state where one side of the detecting coil 2 is placed in a diameter direction of the exciting coil 1, inside the exciting coil 1.

FIGS. 4A and 4B are explanatory views for explaining the path of the eddy current generated on the surface of the test material T. As shown in FIG. 4A, when there is no flaw on the surface of the test material T, the eddy current on the surface of the test material T flows in a circumferential direction equal to the winding direction of the exciting coil 1. In this case, almost no magnetic field is generated in a direction crossing the detecting coil 2 by the eddy current, and therefore almost no electromotive force is generated in the detecting coil 2. Further, in this case, since the output of the detecting coil 2 is substantially zero, even when lift-off changes, the output of the detecting coil 2 contains almost no noise component due to the change in lift-off.

On the other hand, as shown in FIG. 4B, when there is a flaw on the surface of the test material T, the eddy current flows along the flaw. When the detecting coil 2 is parallel to the longitudinal direction of the flaw, as shown in FIG. 3, a magnetic field is generated in the direction crossing the detecting coil 2 by the eddy current, and an electromotive force is generated in the detecting coil 2.

For such reasons, according to the eddy current testing probe reported in the prior art reference, since the output of the detecting coil 2 contains almost no noise component, it is possible to significantly improve the flaw detection accuracy.

However, the above-described eddy current testing probe reported in the prior art reference has a problem that the output of the detecting coil 2 still contains a noise component for reasons explained below.

FIG. 5 is a schematic view for explaining the state of a magnetic field generated around the eddy current testing probe reported in the prior art reference. As shown in FIG. 5, in the eddy current testing probe, since a solenoid coil having a short length relative to the coil diameter is often used as the exciting coil 1, the magnetic field generated by the exciting coil 1 contains not only a magnetic flux perpendicular to the surface of the test material T, but also a magnetic flux curved to the outside of the exciting coil 1 as the distance from the exciting coil 1 in the center axis direction thereof increases.

Accordingly, inside the detecting coil 2, the magnetic field in a direction crossing the detecting coil 2 increases as the distance from the exciting coil 1 increases, and therefore the noise component corresponding to a change in lift-off is contained in the output of the detecting coil 2.

On the other hand, compared to the case where the longitudinal direction of flaw and the detecting coil 2 are parallel, when the longitudinal direction of flaw and the detecting coil 2 are not parallel, the output of the detecting coil 2 decreases. Further, when the longitudinal direction of flaw and the detecting coil 2 are perpendicular, there is a problem that the flaw is undetectable and the flaw detection accuracy is low.

BRIEF SUMMARY OF THE INVENTION

It is an object of the present invention to provide an eddy current testing probe capable of enabling a detecting coil to contain almost no component crossing the detecting coil, of a magnetic field generated by an exciting coil, in the inside of the detecting coil and reducing the noise component corresponding to a change in lift-off, contained in the output of the detecting coil, by positioning the detecting coil obtained by winding a conductor in the shape of a polygon such as a triangle and a pentagon so that one side of the polygon is placed on the exciting coil side and the vertex opposite to the one side is placed apart from the exciting coil.

Another object of the present invention is to provide an eddy current testing probe capable of detecting a flaw in a stable manner, irrespective of the direction of the flaw, by positioning a detecting coil whose center axis is in a direction crossing the center axis direction of an exciting coil on the center axis of the exciting coil and rotating the detecting coil about the center axis of the exciting coil.

Still another object of the present invention is to provide an eddy current testing probe capable of detecting the longitudinal direction of a flaw and accurately detecting the properties of the flaw, including the direction of the flaw relative to the test material, by detecting the rotation angle of the detecting coil.

Yet another object of the present invention is to provide an eddy current testing probe capable of detecting a flaw in a stable manner, irrespective of the longitudinal direction of the flaw, by positioning a plurality of detecting coils whose center axes are in a plurality of different directions respectively crossing the center axis direction of the exciting coil.

A further object of the present invention is to provide an eddy current testing probe capable of obtaining an output voltage indicating the properties of flaw most accurately by selecting the maximum output voltage from the output voltages of a plurality of detecting coils, and thereby improving the flaw detection accuracy.

An eddy current testing probe according to the first aspect of the present invention is an eddy current testing probe comprising: an exciting coil; and a detecting coil whose center axis is in a direction crossing a center axis direction of the exciting coil, wherein the detecting coil is composed of a conductor wound in a shape of a polygon, and positioned by placing one side of the polygon on the exciting coil side and placing a vertex opposite to the one side apart from the exciting coil.

In the state where a side surface of the exciting coil on the side opposite to a vertex of the detecting coil at a distance from the exciting coil (the vertex in a position closer to the inside center of the exciting coil relative to one side of the polygon placed on the exciting coil side) is placed to face a test material, by causing an alternating current to flow in the exciting coil, it is possible to detect a flaw on the surface of the test material. In the detecting coil in the shape of a polygonal ring whose top part space becomes narrower as the distance from the exciting coil in a direction crossing the exciting coil increases, it is possible to make the space inside the detecting coil smaller as the distance from the exciting coil increases, thereby enabling the space inside the detecting coil to contain almost no magnetic field in a direction crossing the detecting coil.

FIGS. 6A and 6B are explanatory views for explaining the direction of the magnetic field in the vicinity of the detecting coil. As shown in FIG. 6A, in the detecting coil 2 in the shape of a quadrangular ring, the distance between two sides placed in the direction crossing the exciting coil 1 is uniform irrespective of the distance from the exciting coil 1. In contrast, as shown in FIG. 6B, in the detecting coil 2 in the shape of a polygonal ring like a triangle ring with the narrowed top part space, the distance between two sides placed in the direction crossing the exciting coil decreases as the distance from the exciting coil 1 increases. Therefore, in the space inside the detecting coil 2 in the shape of a quadrangular ring with four equal angles, in the outside space of a portion distant from the exciting coil 1, a large magnetic field in a direction crossing the detecting coil 2 is contained. On the other hand, in the detecting coil 2 in the shape of a polygonal ring like a triangle ring with the narrowed top space, since the inside space becomes smaller as the distance from the exciting coil 1 increases, almost no magnetic field in a direction crossing the detecting coil 2 is contained in the space inside the detecting coil 2. The magnetic field in the direction crossing the detecting coil 2 induces a voltage between the terminals of the detecting coil 2, and the strength of such a magnetic field varies according to a change in lift-off. Therefore, the induced voltage also changes according to a change in lift-off, causing a noise component. Accordingly, in the eddy current testing probe of the first aspect, it is possible to reduce the noise component corresponding to a change in lift-off, contained in the output of the detecting coil 2.

An eddy current testing probe of the second aspect of the present invention is based on an eddy current testing probe comprising an exciting coil and a detecting coil, and the detecting coil is positioned on the center axis of the exciting coil so that a center axis of the detecting coil is in a direction crossing a center axis direction of the exciting coil and the detecting coil is rotatable about the center axis of the exciting coil.

The detecting coil whose center axis is in a direction crossing the center axis direction of the exciting coil is positioned on the center axis of the exciting coil, and the detecting coil is rotated about the center axis of the exciting coil. When the detecting coil and the longitudinal direction of a flaw become parallel to each other, the maximum output voltage is generated in the detecting coil. The output voltage generated at this moment accurately indicates the properties of the flaw. Therefore, by obtaining this output voltage, it is possible to detect a flaw accurately and detect a flaw in a stable manner irrespective of the longitudinal direction of the flaw.

In the eddy current testing probe of the second aspect, the rotation angle of the detecting coil is detected. During one rotation of the detecting coil, when the maximum output voltage is generated, the detecting coil and the flaw are parallel. By obtaining the rotation angle of the detecting coil at this moment, it is possible to detect the longitudinal direction of the flaw and accurately detect the properties of the flaw, including the direction of the flaw relative to the test material.

An eddy current testing probe of the third aspect of the present invention is based on an eddy current testing probe comprising an exciting coil and a plurality of detecting coils, and the respective detecting coils are positioned on the center axis of the exciting coil so that center axes of the detecting coils are in a plurality of different directions respectively crossing a center axis direction of the exciting coil.

The plurality of detecting coils whose center axes are in a plurality of different directions respectively crossing the center axis direction of the exciting coil are positioned on the center axis of the exciting coil. Consequently, irrespective of the orientation of the longitudinal direction of a flaw, it is possible to detect the flaw with a detecting coil which is substantially parallel to the flaw. It is thus possible to detect a flaw in a stable manner, irrespective of the longitudinal direction of the flaw.

In the eddy current testing probe of the third aspect, the maximum output voltage is selected from the output voltages of the plurality of detecting coils. A detecting coil generates the maximum output voltage when the detecting coil becomes parallel to a flaw. Accordingly, the detecting coil generating the maximum output voltage is in a position more parallel to the flaw than the other detecting coils, and this output voltage indicates the properties of the flaw more accurately than the other output voltages. Therefore, a selected output voltage accurately shows the properties of flaw, and such a structure can improve the flaw detection accuracy.

The above and further objects and features of the invention will more fully be apparent from the following detailed description with accompanying drawings.

DETAILED DESCRIPTION OF THE INVENTION

The following description will explain the present invention in detail, based on the drawings illustrating some embodiments thereof.

(First Embodiment)

Figure 1:
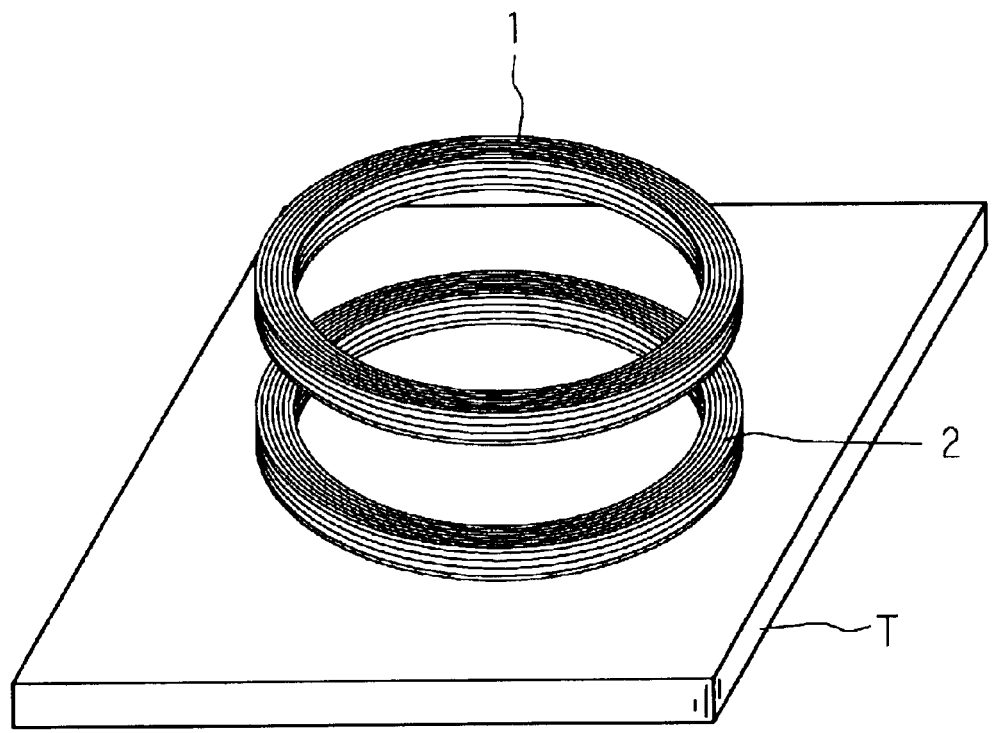
FIG. 1 is a schematic view showing schematically the configuration of a conventional general eddy current testing probe.
Figure 2:
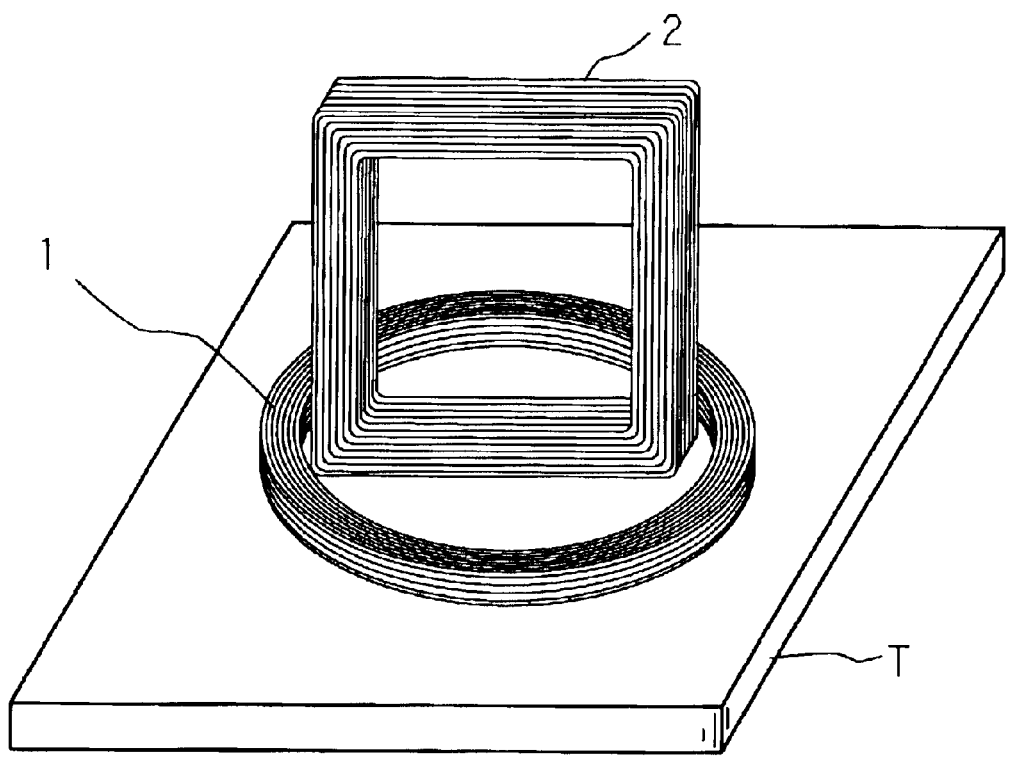
FIG. 2 is a schematic view showing schematically the configuration of an eddy current testing probe reported in a prior art reference.
Figure 3:
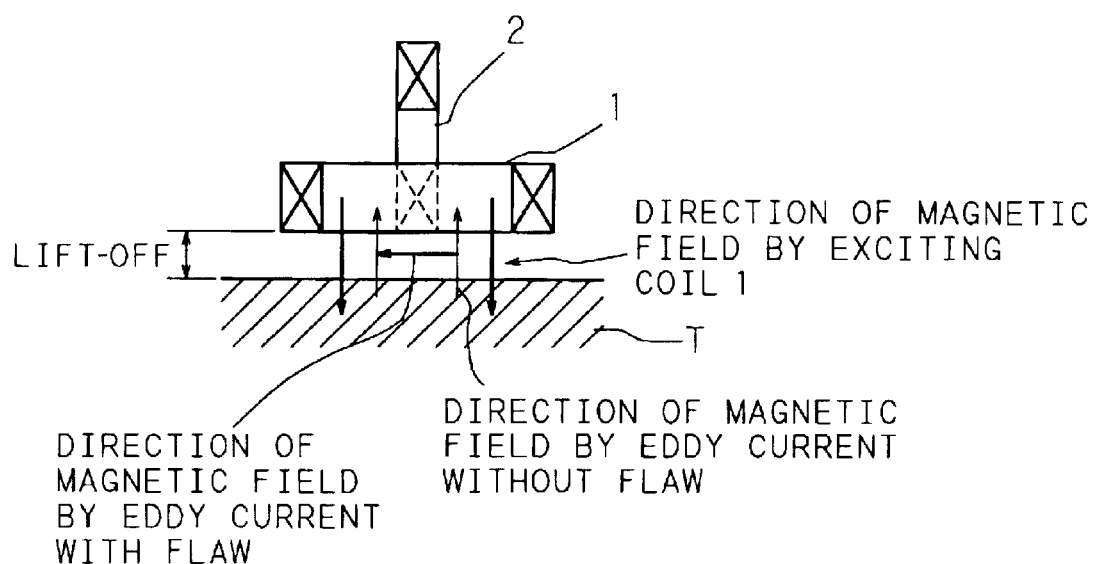
FIG. 3 is an explanatory view for explaining the operational principle of the eddy current testing probe reported in the prior art reference.
Figure 4A:
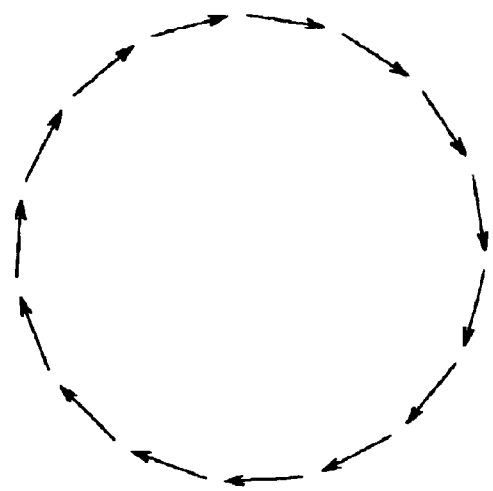
FIGS. 4A and 4B are views for explaining the path of an eddy current generated on the surface of a test material.
Figure 4B:
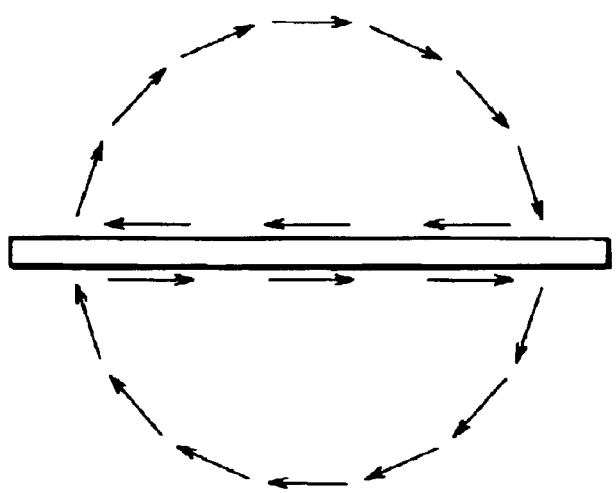
Figure 5:
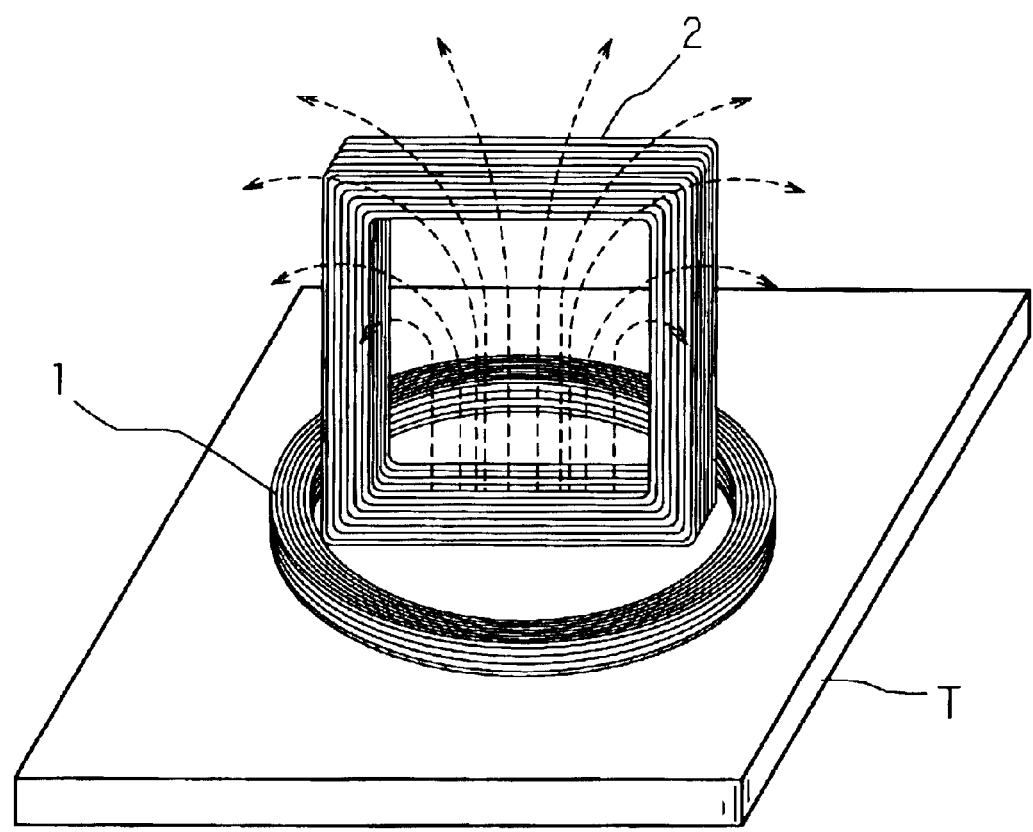
FIG. 5 is a schematic view for explaining the state of a magnetic field generated around the eddy current testing probe reported in the prior art reference.
Figure 6A:
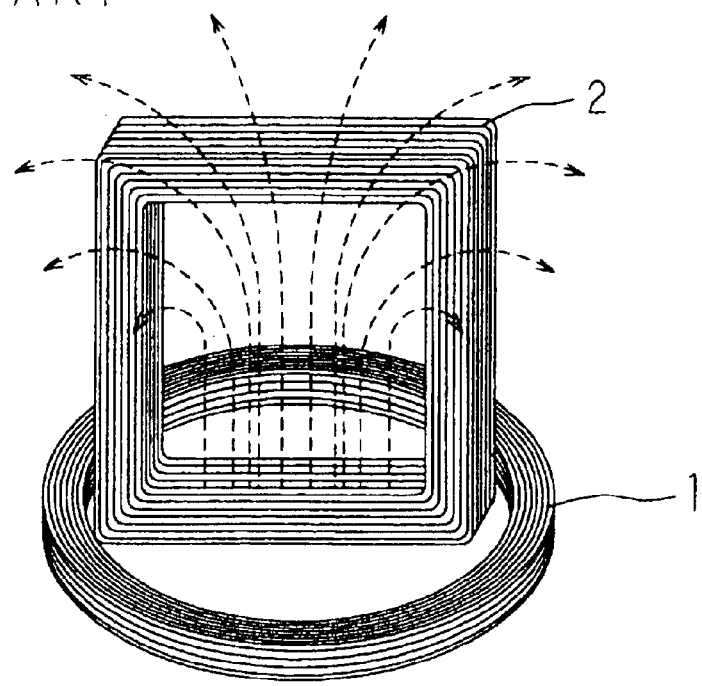
FIGS. 6A and 6B are explanatory views for explaining the direction of the magnetic field in the vicinity of a detecting coil.
Figure 6B:
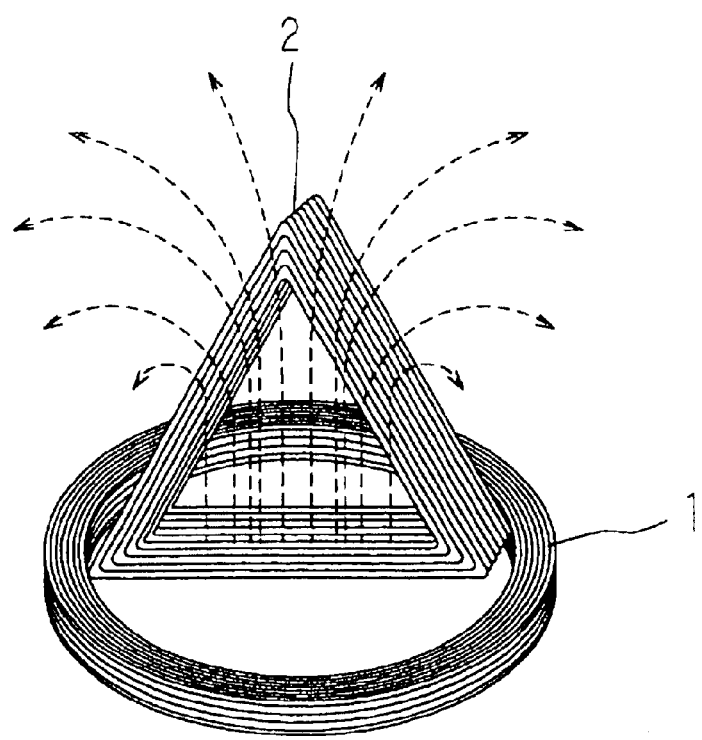
Figure 7:
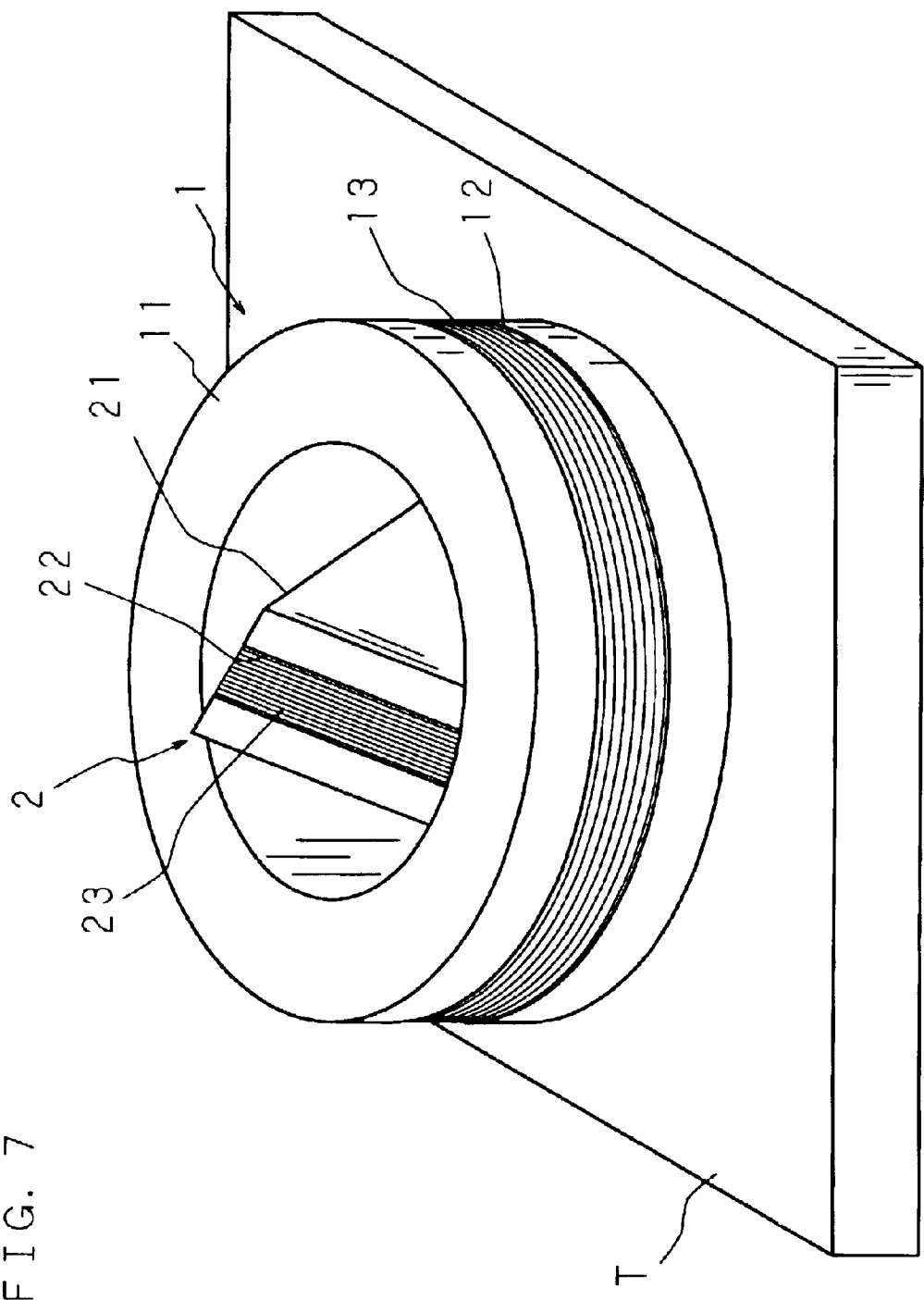
FIG. 7 is a perspective view showing the structure of essential parts of an eddy current testing probe of the first embodiment.
Figure 8:
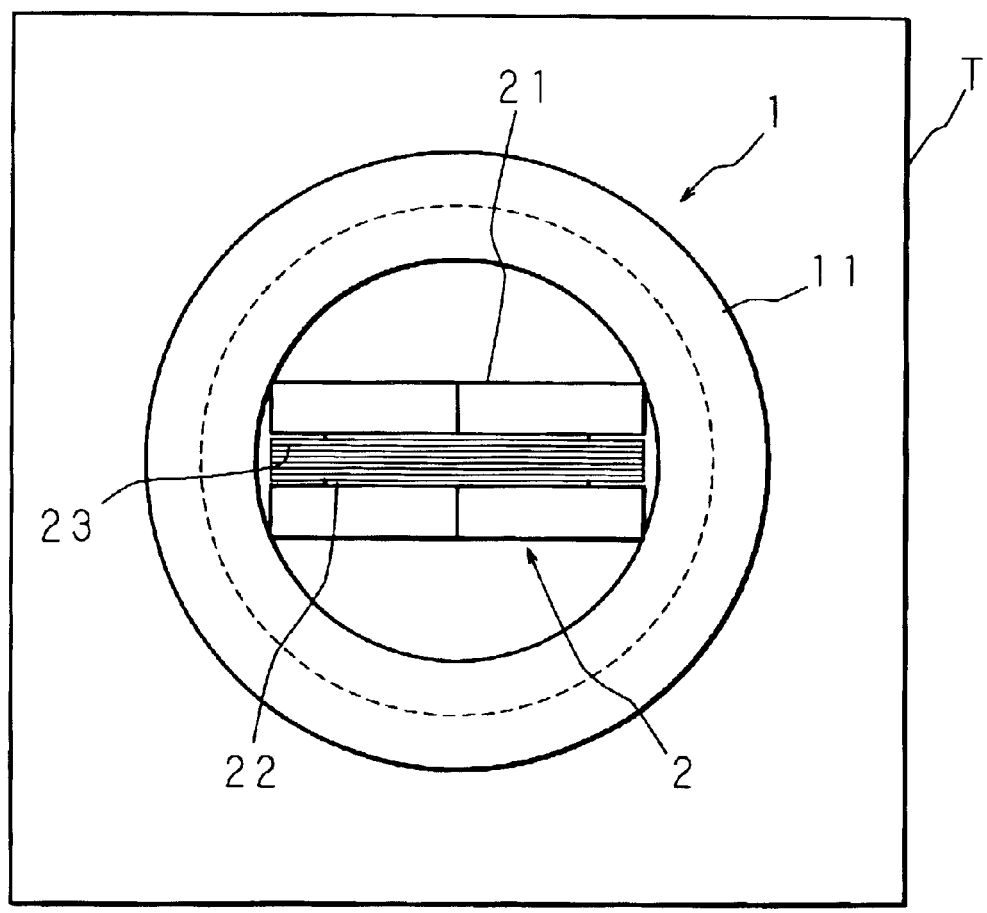
FIG. 8 is a plan view showing the structure of essential parts of the eddy current testing probe of the first embodiment.
Figure 9:
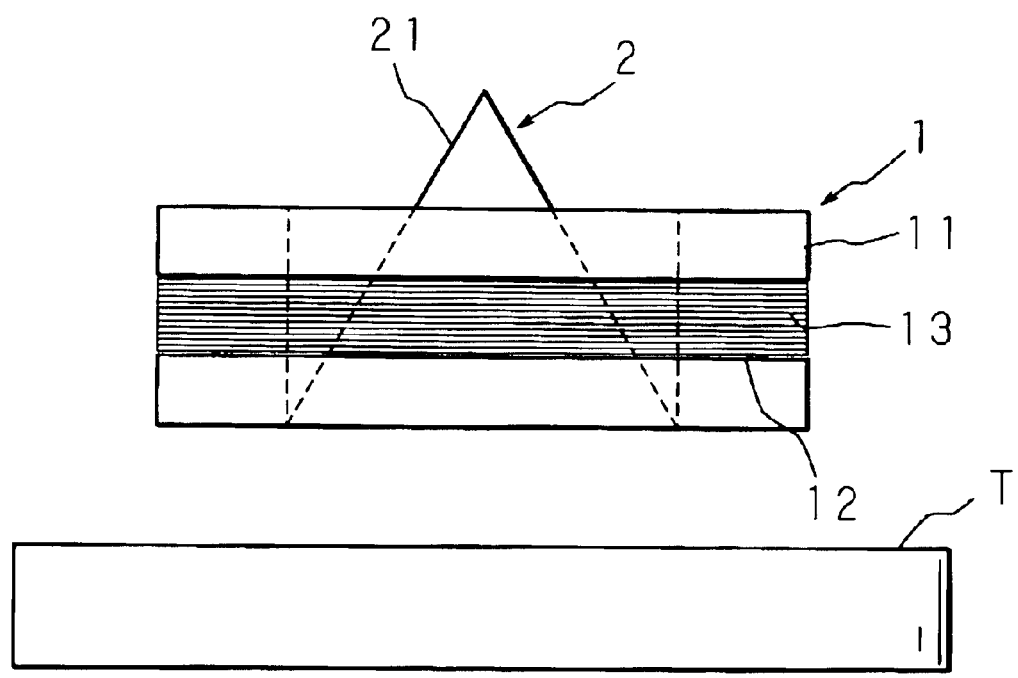
FIG. 9 is a front view showing the structure of essential parts of the eddy current testing probe of the first embodiment.

FIGS. 7, 8 and 9 are the perspective view, plan view and front view showing the structure of essential parts of an eddy current testing probe of the first embodiment. In these FIG. 1 is an exciting coil, and 2 is a detecting coil. The exciting coil 1 is constructed by forming circumferentially a groove 12 with a width of 1 mm and a depth of 1.5 mm on the outer circumference of a polycarbonate circular ring member 11 with an outside diameter of 12 mm, an inside diameter of 6 mm and a thickness of 5 mm and winding 120 turns a winding 13 with an outside diameter of 300 $\mu$m, made of a copper wire coated with a polyimide resin, in the groove 12.

Meanwhile, the detecting coil 2 is constructed by forming circumferentially a groove 22 with a width of 1 mm and a depth of 1 mm on the outer circumference of a 3 mm-thick polycarbonate triangular member 21, which is in the shape of an equilateral triangle with a side length slightly smaller than 6 mm when seen from the front, and winding 100 turns a winding 23 with an outside diameter of 70 $\mu$m, made of a copper wire coated with a polyimide resin, in the groove 22.

Note that while the exciting coil 1 has a circular ring shape, the shape is not necessarily limited to this, and, needless to say, the exciting coil 1 may have other shape such as a quadrangular ring shape or a triangular ring shape. Moreover, while the triangular member 21 is in the shape of an equilateral triangle when seen from the front, the shape is not necessarily limited to this, and, needless to say, the triangular member 21 may be in the shape of an isosceles triangle, for example, when seen from the front.

Such a detecting coil 2 is positioned perpendicular to the exciting coil 1, and its one side is inserted into the circular ring member 11 of the exciting coil 1 until the lower surface of the detecting coil 2 aligns with the lower surface of the exciting coil 1.

Needless to say, the exciting coil 1 and the detecting coil 2 are not necessarily limited to the above-mentioned dimensions and material, and other dimensions and materials may be used.

The eddy current testing probe constructed as described above is positioned so that its lower surface functioning as the flaw detection surface faces the surface of a test material T in the shape of a flat plate, for example, with an appropriate distance from the test material T, and is used by scanning the surface of the test material T in this state.

Figure 10:
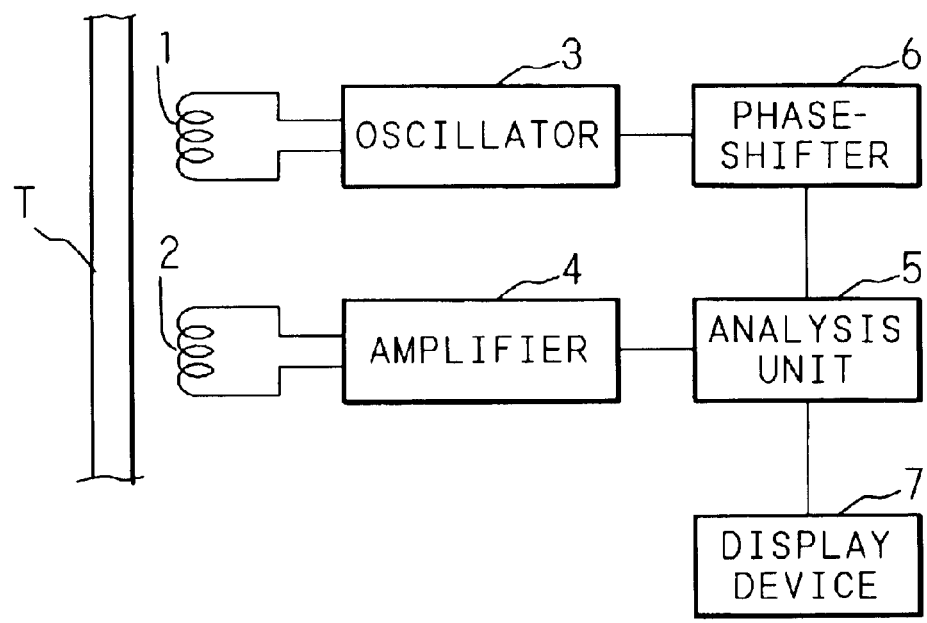
FIG. 10 is a block diagram showing the configuration of an eddy current testing device using an eddy current testing probe (the first and second embodiments) of the present invention.

FIG. 10 is a block diagram showing the configuration of an eddy current testing device using the eddy current testing probe of the first embodiment. The exciting coil 1 is connected to an oscillator 3, so that an alternating current produced by the oscillator 3 is supplied to the exciting coil 1. Besides, the detecting coil 2 is connected to an amplifier 4, so that the output from the detecting coil 2 is amplified. The amplifier 4 is connected to an analysis unit 5 composed of a CPU, memory, etc. The output from the amplifier 4 is converted into a digital signal by an A/D converter (not shown) incorporated in the analysis unit 5, and processed by the CPU.

Meanwhile, the output from the oscillator 3 is phase-shifted by a predetermined amount by a phase-shifter 6, and then supplied to the analysis unit 5. Like the output from the amplifier 4, the output from the phase-shifter 6 is also converted into a digital signal by the A/D converter incorporated in the analysis unit 5, and then supplied to the CPU. The analysis unit 5 performs a phase-analysis using a known technique, based on the signal outputted from the amplifier 4 and the signal outputted from the phase-shifter 6. The result of the analysis is displayed on a display device 7 such as a CRT connected to the analysis unit 5.

In the above-described configuration, the alternating current is supplied from the oscillator 3 to the exciting coil 1, and a magnetic field is generated around the exciting coil 1. When there is no flaw on the surface of the test material T, an eddy current in the same direction as the winding direction of the exciting coil 1 flows on the surface of the test material T, and a magnetic field is generated by this eddy current.

The detecting coil 2 is positioned perpendicular to the test material T, and the space inside the detecting coil 2 becomes smaller as the distance from the test material T increases. Therefore, almost no magnetic field crossing the detecting coil 2 is generated by the eddy current flowing in the same direction as the winding direction of the exciting coil 1. Accordingly, almost no electromotive force is generated in the detecting coil 2, and the output from the amplifier 4 becomes substantially zero.

Besides, when lift-off changes, the strength of the magnetic field generated in the vicinity of the surface of the test material T by the exciting coil 1 varies. Therefore, the strength of the eddy current generated on the test material T changes, and the strength of the magnetic field generated by the eddy current varies. However, since the magnetic field generated by the eddy current hardly crosses the detecting coil 2, almost no electromotive force is generated in the detecting coil 2, and the output from the amplifier 4 is still substantially zero. Consequently, the output of the detecting coil 2 contains almost no noise component caused by lift-off.

On the other hand, when there is a flaw on the surface of the test material T, the eddy current flows along the flaw, and the strength and direction of a magnetic field due to the eddy current change relative to the strength and direction of a magnetic field caused by the eddy current flowing when no flaw is present on the surface of the test material T. Consequently, the magnetic field crosses the detecting coil 2, an electromotive force is generated in the detecting coil 2, and the output from the amplifier 4 changes.

(Second Embodiment)

Figure 11:
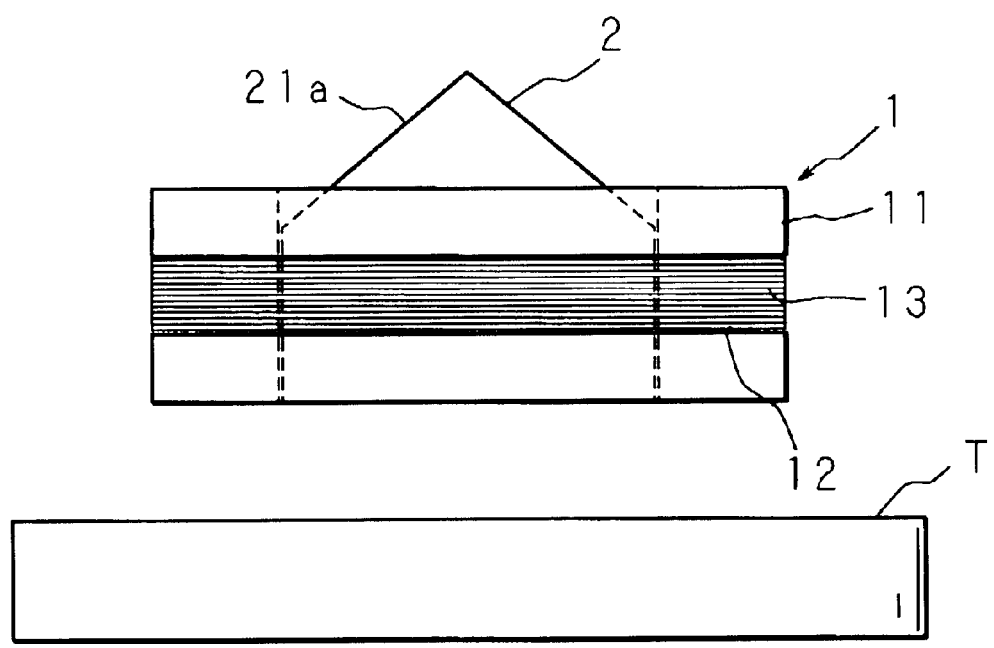
FIG. 11 is a front view showing the structure of essential parts of an eddy current testing probe of the second embodiment.

FIG. 11 is a front view showing the structure of essential parts of an eddy current testing probe of the second embodiment. Since the second embodiment is basically the same as the first embodiment, the same reference numbers are designated and detailed explanation is omitted. The difference is that the detecting coil 2 is in the form of a house-shaped pentagon when seen from the front, and a polygonal member 21a in the shape of a pentagon is used and a winding (see 23 of FIGS. 7 and 8) is wound around the polygonal member 21a. Hence, by positioning the detecting coil 2 so that one side of the polygon is placed on the exciting coil 1 side and the vertex opposite to the one side is placed apart from the exciting coil 1, it is possible to obtain similar functions and effects as the first embodiment. In other words, in the detecting coil 2 in the form of a house-shaped pentagonal ring, since the inside space becomes smaller as the distance from the exciting coil 1 increases, it is possible to enable the space inside the detecting coil 2 to contain almost no magnetic field in the direction crossing the detecting coil 2.

Regarding the polygon shape of the detecting coil 2, in order to make the top part (inside space) distant from the exciting coil 1 small as described above, a polygon with an odd number of sides is preferred to a polygon with an even number of sides as it is more easily constructed. However, if it is possible to make the inside space smaller according to the distance from the exciting coil 1 in the crossing direction, the shape is not necessarily limited to a polygon with an odd number of sides, and the detecting coil 2 may have, for example, a trapezoid shape with the upper side (the side distant from the exciting coil 1) shorter than the lower side. In the case of the trapezoid shape, there are two vertexes opposite to one side placed on the exciting coil 1 side. In this case, the respective vertexes are also placed apart from the exciting coil 1 inward. Note that since the above-described effect is not obtained by a quadrangle (square) with four equal angles, this shape is, of course, excluded from the polygon mentioned here. Moreover, from a manufacturing standpoint, although polygon with three or more angles is available, polygon with four or more angles and the narrower top such as trapezoid has the advantages of easy winding of coil and less risk of disconnection compared to triangle.

(Third Embodiment)

Figure 12:
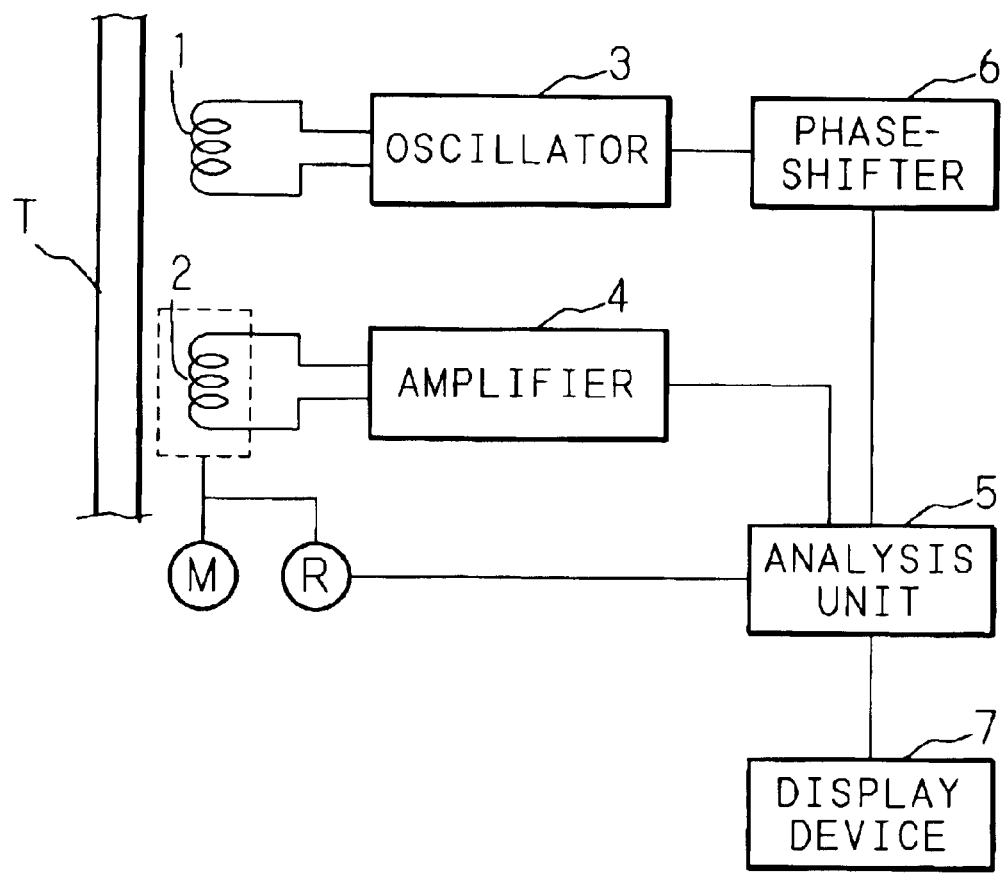
FIG. 12 is a block diagram showing the configuration of an eddy current testing device using an eddy current testing probe (the third embodiment) of the present invention.

FIG. 12 is a block diagram showing the configuration of an eddy current testing device using an eddy current testing probe of the third embodiment. The detecting coil 2 is connected to the rotation shaft of a motor M arranged coaxially with the exciting coil 1 so that it is rotatable about the center axis of the exciting coil 1. Moreover, the detecting coil 2 is connected to a rotary encoder R, and the rotary encoder R is connected to the analysis unit 5 so as to detect the rotation angle of the detecting coil 2.

In the analysis unit 5, upon the receipt of the output from the rotary encoder R, the rotation angle of the detecting coil 2 is computed. Then, the maximum output is extracted from the outputs of the amplifier 4 obtained during one rotation of the detecting coil 2, and the phase-analysis is performed using this output. The result of the analysis is outputted to the display device 7 together with the rotation angle of the detecting coil 2.

Since other structures of the eddy current testing probe and eddy current testing device of the third embodiment are the same as those of the eddy current testing probe and eddy current testing device of the first embodiment, they are designated with the same reference numbers, and the explanation thereof is omitted.

Note that, in the third embodiment, while the detecting coil 2 has a triangular ring shape, the shape is not necessarily limited to this, and, needless to say, the detecting coil 2 may have other shape such as a quadrangular ring shape, pentagonal ring shape or a circular ring shape. Moreover, in the third embodiment, while the detecting coil 2 is rotatable about the center axis of the exciting coil 1, the detecting coil 2 is not necessarily limited to this structure, and may be arranged to be swingable about the center axis of the exciting coil 1.

(Fourth Embodiment)

Figure 13:
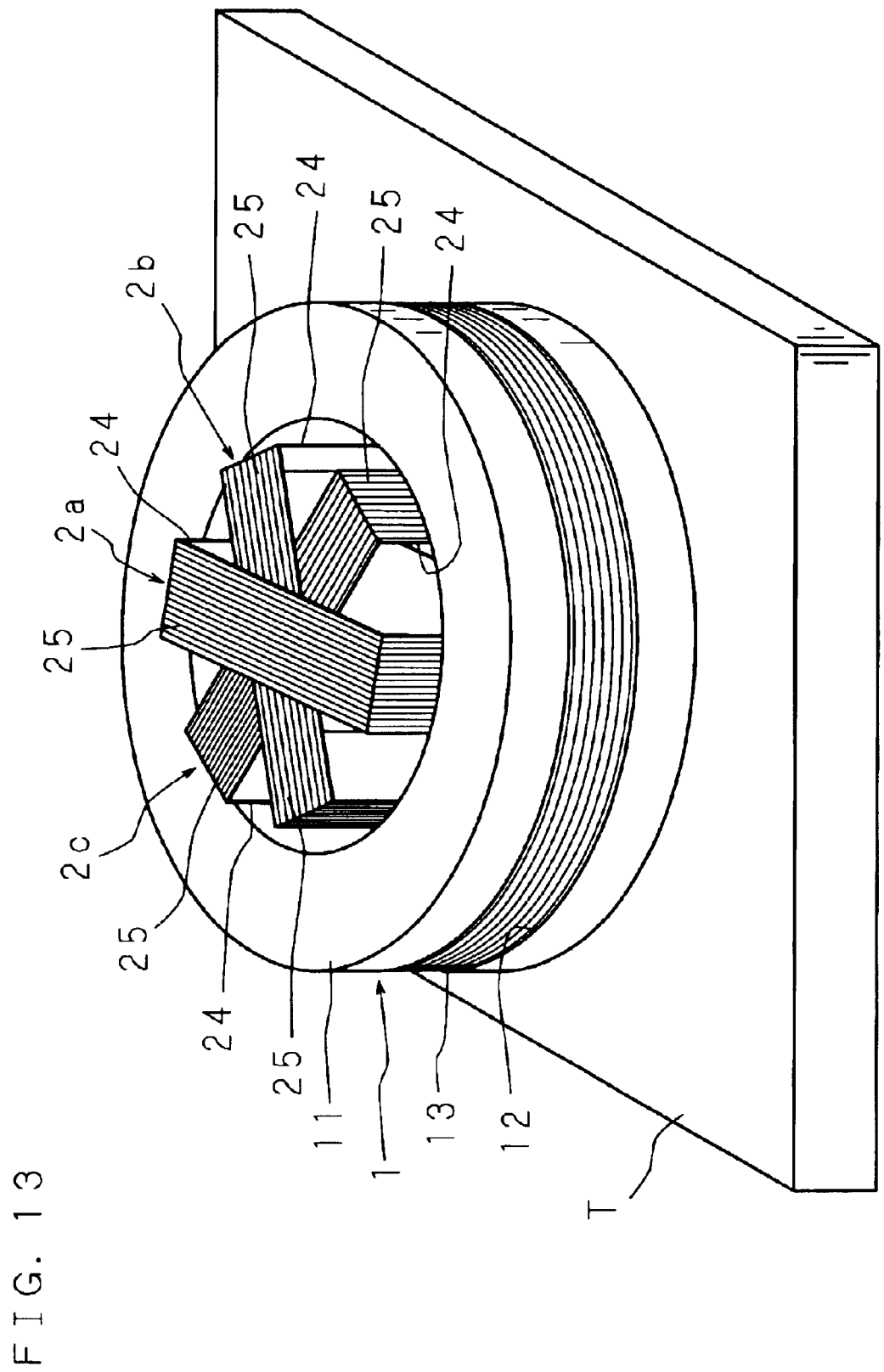
FIG. 13 is a perspective view showing the structure of essential parts of an eddy current testing probe of the fourth embodiment.

FIG. 13 is a perspective view showing the structure of essential parts of an eddy current testing probe of the fourth embodiment. The dimensions of the circular ring member 11 are 10 mm in outside diameter, 6 mm in inside diameter, and 3 mm in thickness. Since other structures of the exciting coil 1 of the fourth embodiment are the same as the exciting coil 1 of the first embodiment, they are designated with the same reference numbers, and the explanation thereof is omitted.

Besides, the eddy current testing probe of the fourth embodiment has three detecting coils 2a, 2b and 2c. Each of the detecting coils 2a, 2b and 2c has a square ring shape, and is constructed by forming 100 turns of winding 25 with a thickness of 5 $\mu$m, a line width of 3 $\mu$m and a line spacing of 3 $\mu$m in a quadrangle member 24 produced by winding a strip of film with a width of 1 mm and a thickness of 50 $\mu$m into a square shape with a side length of 5 mm.

The film is composed of two sheets of polyimide films bonded together, and each winding 25 is formed by bonding a 5 $\mu$m-thick copper foil onto one of the polyimide films and etching the copper foil. Then, this polyimide film with copper foil is bonded to the other polyimide film with the winding 25 therebetween and bent into a square shape to form each of the detecting coils 2a, 2b and 2c.

The detecting coils 2a, 2b and 2c thus constructed are arranged at an interval of 60° between the respective detecting coils 2a, 2b and 2c in such a state that the center portions of the upper sides of the respective detecting coils 2a, 2b and 2c overlap each other in the order of the detecting coils 2a, 2b and 2c downward and the center portions of the respective lower sides overlap each other in the order of the detecting coils 2a, 2b and 2c downward.

Note that, in the fourth embodiment, while the overlapping order of the upper sides of the detecting coils 2a, 2b and 2c and the overlapping order of the lower sides are the same, the orders are not necessarily limited to this, and, needless to say, the overlapping order of the upper sides of the detecting coils 2a, 2b and 2c and the overlapping order of the lower sides may differ from each other. Further, in the fourth embodiment, while the number of the detecting coils is three, the number is not necessarily limited to this, and two detecting coils, or four or more detecting coils may be used. Besides, in the fourth embodiment, while the detecting coil has a quadrangular ring shape, the shape is not necessarily limited to this, and, needless to say, the detecting coil may have other shape such as a triangular ring shape, pentagonal ring shape or a circular ring shape.

Figure 14:
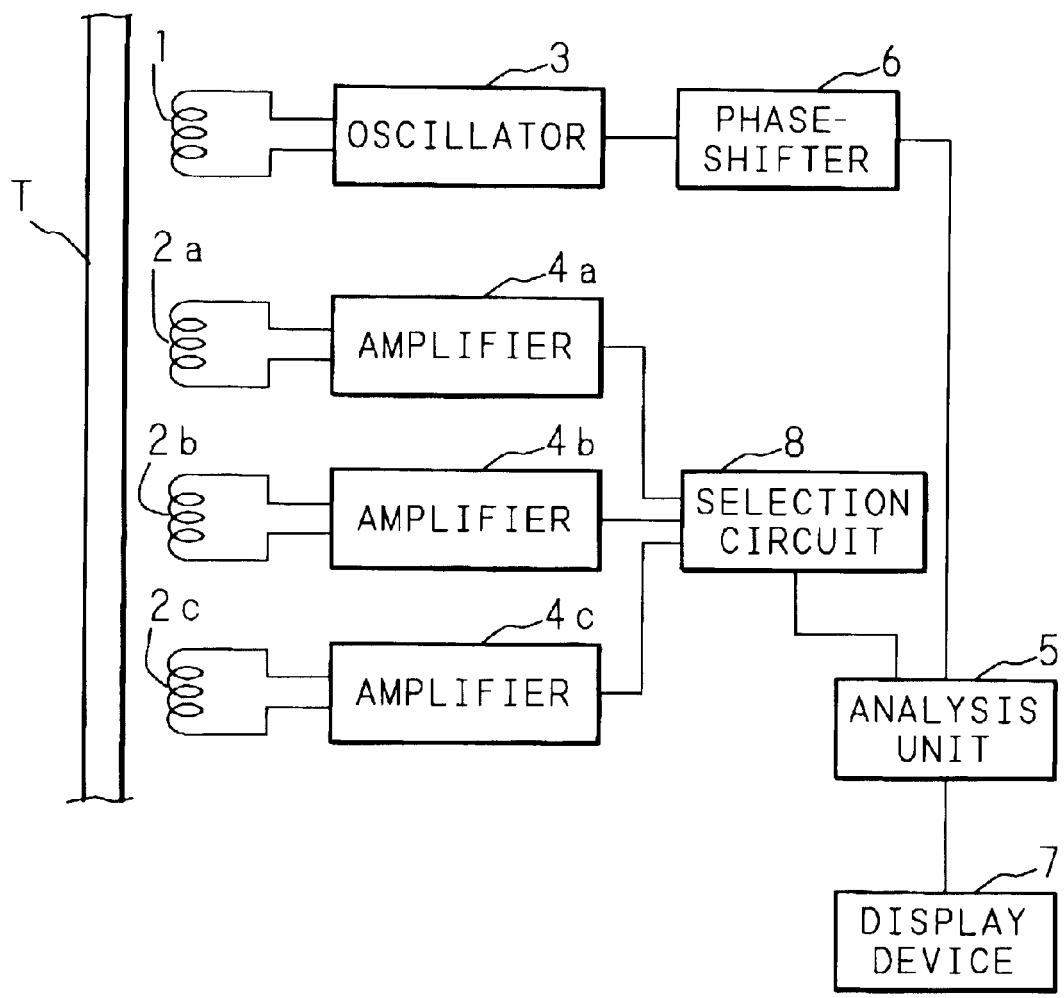
FIG. 14 is a block diagram showing the configuration of an eddy current testing device using the eddy current testing probe (the fourth embodiment) of the present invention.

FIG. 14 is a block diagram showing the configuration of an eddy current testing device using the eddy current testing probe of the fourth embodiment. The detecting coils 2a, 2b and 2c are connected to amplifiers 4a, 4b and 4c, respectively, and the amplifiers 4a, 4b and 4c are connected to a selection circuit 8 composed of a CPU, memory, etc. The outputs of the amplifiers 4a, 4b and 4c are converted into digital signals by an A/D converter (not shown) incorporated in the selection circuit 8, and then supplied to the CPU. The CPU judges which is the maximum output among the outputs of the amplifiers 4a, 4b and 4c, selects the maximum output, and outputs it to the analysis unit 5.

Since other structures of this eddy current testing device are the same as those of the above-mentioned eddy current testing device shown in FIG. 10, they are designated with the same reference numbers, and the explanation thereof is omitted.

Comparative experiments were performed for the eddy current testing probe of the fourth embodiment and an eddy current testing probe reported in the prior art reference (hereinafter referred to as the "conventional eddy current testing probe"). The conventional eddy current testing probe was constructed by positioning a detecting coil having the same shape as the detecting coil 2a of the fourth embodiment orthogonally to an exciting coil having the same shape as the exciting coil 1 of the fourth embodiment so that one side of the detecting coil was placed in a diameter direction of the exciting coil, inside the exciting coil.

Figure 15:
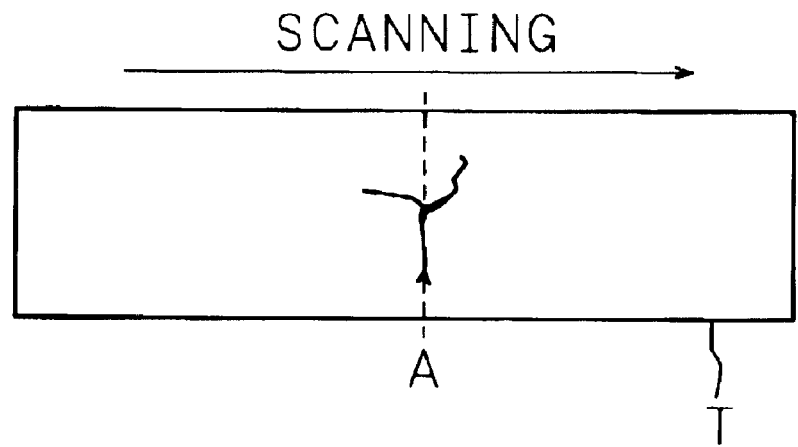
FIG. 15 is a plan view showing the structure of a test material used in experiments.

FIG. 15 is a plan view showing the structure of a test material T used in the experiments. The test material T was a steel plate in a rectangular parallelepiped shape in the plan view and having flaws extending in three directions from the center portion thereof (a portion shown by A in FIG. 15). The experiments were carried out by scanning the conventional eddy current testing probe and the eddy current testing probe of the fourth embodiment in the direction shown by the arrow. Note that, in the flaw detection by the conventional eddy current testing probe, the detecting coil was positioned perpendicular to the scanning direction.

Figure 16A:
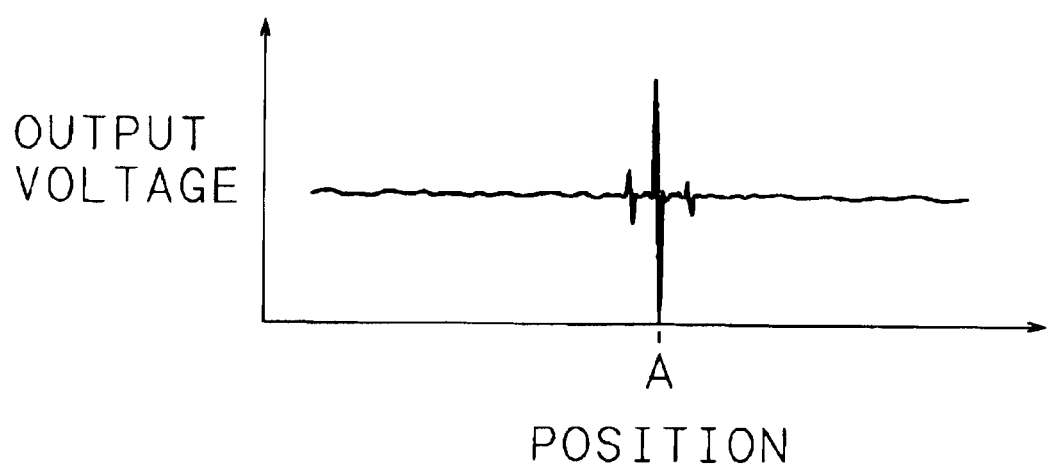
FIGS. 16A and 16B are graphs showing the results of the experiments.
Figure 16B:
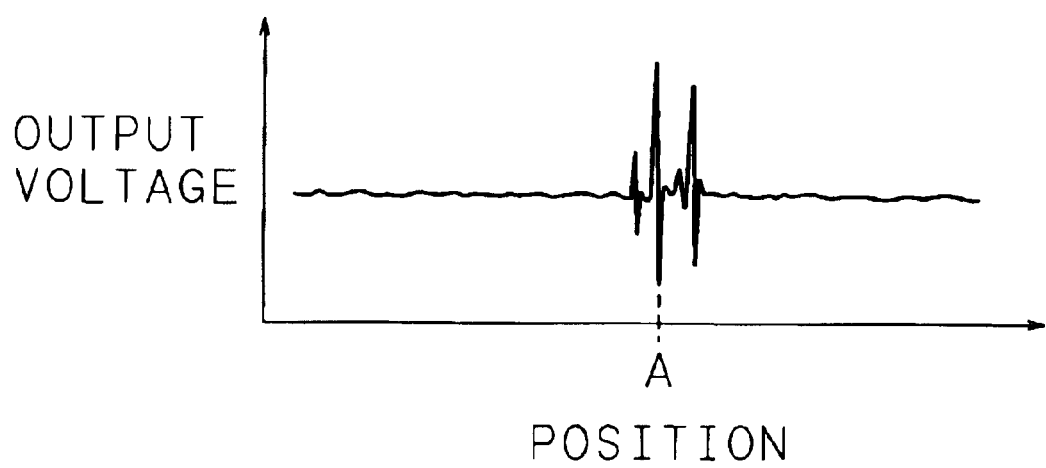

FIGS. 16A and 16B are graphs showing the results of the experiments. In these figures, the abscissa shows the position in the scanning direction, while the ordinates shows the output voltage of the detecting coil. In the flaw detection by the conventional eddy current testing probe, as shown in FIG. 16A, the output of the detecting coil changes significantly in the portion A, but has almost no change in other portions. Therefore, it can be understood that the probe detects only a flaw in the portion A, extending in a direction orthogonal to the scanning direction, i.e., in a direction parallel to the detecting coil.

On the other hand, in the flaw detection by the eddy current testing probe of the fourth embodiment, as shown in FIG. 16B, the output changes significantly not only in the portion A, but also in front of and behind the portion A. Hence, it can be understood that the probe detects not only a flaw extending in a direction parallel to the detecting coil, but also flaws extending in other directions.

As described above, according to the present invention, by placing one side of the polygon of the detecting coil in the shape of a polygonal ring whose inside space becomes narrower as the distance from the exciting coil in a direction crossing the exciting coil increases, on the exciting coil side and placing the vertex opposite to the one side apart from the exciting coil, it is possible to make the space inside the detecting coil smaller as the distance from the exciting coil in a direction crossing the exciting coil increases. Therefore, almost no magnetic field in a direction crossing the detecting coil is contained in the space inside the detecting coil, and it becomes possible to reduce the noise component corresponding to a change in lift-off, contained in the output of the detecting coil.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. An eddy current testing probe comprising:
   an exciting coil having a center axis direction generally perpendicular to a plane of said exciting coil; and
   a detecting coil whose center axis is in a direction crossing the center axis direction of said exciting coil,
   wherein said detecting coil comprises a conductor wound in a shape of a polygon, and is positioned by placing one side of the polygon generally parallel to the plane of the exciting coil and placing a vertex of the polygon adjacent to the center axis of said exciting coil.

2. The eddy current testing probe of claim 1, wherein the polygon is a triangle.

3. The eddy current testing probe of claim 1, wherein the polygon is a pentagon.

4. The eddy current testing probe of claim 1, further comprising a rotator for rotating said detecting coil about the center axis of said exciting coil.

5. The eddy current testing probe of claim 4, further comprising a detector for detecting a rotation angle of said detecting coil.

6. An eddy current testing probe comprising:

an exciting coil; and a detecting coil whose center axis is in a direction crossing a center axis direction of said exciting coil;

wherein said detecting coil comprises a conductor wound in a shape of a polygon, and is positioned by placing one side of the polygon generally parallel to a plane of the exciting coil and placing a vertex opposite to the one side, apart from said exciting coil; and wherein the polygon is a triangle.

7. The eddy current testing probe of claim 6, further comprising a rotator for rotating said detecting coil about the center axis of said exciting coil.

8. The eddy current testing probe of claim 6, further comprising a detector for detecting a rotation angle of said detecting coil.

9. An eddy current testing probe comprising:

an exciting coil; and a detecting coil whose center axis is in a direction crossing a center axis direction of said exciting coil;

wherein said detecting coil comprises a conductor wound m a shape of a polygon, and is positioned by placing one side of the polygon generally parallel to a plane of the exciting coil and placing a vertex opposite to the one side, apart from said exciting coil; and wherein the polygon is a pentagon.

10. The eddy current testing probe of claim 9, further comprising a rotator for rotating said detecting coil about the center axis of said exciting coil.

11. The eddy current testing probe of claim 9, further comprising a detector for detecting a rotation angle of said detecting coil.

* * * * *